United States Patent [19]

Worthington et al.

[11] Patent Number: 4,777,176

[45] Date of Patent: Oct. 11, 1988

[54] FUNGICIDAL COMPOSITIONS CONTAINING PIPERIDINE COMPOUNDS

[75] Inventors: Paul A. Worthington, Maidenhead; Brian K. Snell, Reading; Paul DeFraine, Wokingham; Vivienne M. Anthony, Maidenhead, all of England

[73] Assignee: Imperial Chemical Industries PLC, London, England

[21] Appl. No.: 872,501

[22] Filed: Jun. 10, 1986

[30] Foreign Application Priority Data

Jun. 18, 1985 [GB] United Kingdom ............. 8515386

[51] Int. Cl.$^4$ ............................................. A01N 43/40
[52] U.S. Cl. ........................................ 514/319; 514/649; 514/239.5; 544/178; 546/205; 71/88; 71/94
[58] Field of Search .............. 546/205; 514/319; 424/45; 71/94

[56] References Cited

U.S. PATENT DOCUMENTS 4,022,791  5/1977  Welch, Jr. .................. 544/178
4,130,646  12/1978  Vogt et al. ................. 544/392

FOREIGN PATENT DOCUMENTS 1249261  11/1971  United Kingdom .
1547597  6/1979  United Kingdom .

Primary Examiner—Robert W. Ramsuer

Attorney, Agent, or Firm—Cushman, Darby & Cushman

[57] ABSTRACT

This invention provides fungicidal compositions comprising as an active ingredient a compound having the general formula (I):

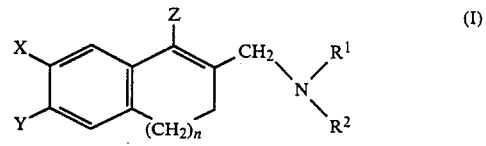

or a stereoisomer thereof, wherein one of X and Y represents hydrogen and the other represents the group

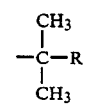

in which R is hydrogen, methyl or ethyl; Z represents hydrogen or an alkyl group containing from one to four carbon atoms; $R^1$ and $R^2$, which may be the same or different, represent hydrogen or an alkyl group containing one to four carbon atoms, or $R^1$ and $R^2$ together with the adjacent nitrogen atom represent an optionally-substituted heterocyclic ring; and n is 0 or 1.

4 Claims, No Drawings

FUNGICIDAL COMPOSITIONS CONTAINING PIPERIDINE COMPOUNDS

This invention relates to fungicidal compositions containing organic amine compounds, and to methods of using them to combat fungi, especially fungal infections in plants; the invention also relates to certain of those compounds which are novel per se.

This invention provides fungicidal compositions comprising as an active ingredient a compound having the general formula (I):

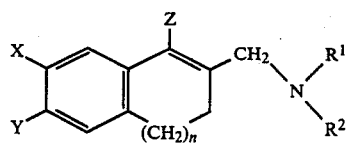

or a stereoisomer thereof, wherein one of X and Y represents hydrogen and the other represents the group

in which R is hydrogen, methyl or ethyl; Z represents hydrogen or an alkyl group containing from one to four carbon atoms; $R^1$ and $R^2$, which may be the same or different, represent hydrogen or an alkyl group containing one to four carbon atoms, or $R^1$ and $R^2$ together with the adjacent nitrogen atom represent an optionally-substituted heterocyclic ring; and n is 0 or 1.

Preferably $R^1$ and $R^2$, together with the adjacent N-atom, represent the residue of a tertiary amine, and it is further preferred that they represent a heterocyclic ring; this may be, for example, a piperidine, pyrrolidine, piperazine or morpholine ring which may be optionally substituted by one or more groups alkyl (itself optionally substituted) containing one to four carbon atoms, aryl (itself optionally substituted), hydroxy, alkoxy, or aryloxy (itself optionally substituted) or aralkyl (itself optionally substituted).

Particularly preferred heterocyclic rings which are thus represented are the piperidine and 2,6-dimethylmorpholine ring systems.

It is also preferred that one of X and Y should be a tert-butyl group, that is to say, it should have the structure defined above where R is a methyl group.

It is further preferred that Z should be hydrogen or a methyl group.

The invention further provides fungicidal compositions comprising salts of the above compounds of general formula (I) with inorganic or organic acids. Examples of salts are those with hydrochloric, nitric, sulphuric, acetic, 4-toluene-sulphonic or oxalic acid.

U.S. Pat. No. 4130646 generically describes the pharmaceutical use as sedatives and tranquillisers of certain classes of compound including those having the general formula

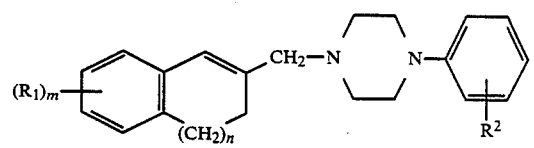

where, inter alia, $R_1$ may be hydrogen or alkyl, m is 1 or 2 and n may be 0 or 1. There is, however, no reference to these compounds possessing fungicidal activity and the majority of them differ from the compounds defined by formula (I) above in not showing the specified values for X and Y.

Examples of compounds conforming to formula (I) which may be incorporated in the compositions of the invention are shown in Table I.

TABLE I (I)

| Compound Number | X | Y | Z | n | NR¹R² | Melting Point (°C.) | Comments | ¹H NMR shifts (ppm from TMS) |
|---|---|---|---|---|---|---|---|---|
| 1 | H | t-C₄H₉ | H | 1 | —N(piperidine) | Oil | | 6.24, 1Hs* 1.23, 9Hs* |
| 2 | H | t-C₄H₉ | H | 1 | —N(2,6-dimethylmorpholine) | Oil | Cis-dimethyl-morpholine | 6.23, 1Hs+ 1.31, 9Hs* |
| 3 | H | t-C₄H₉ | CH₃ | 1 | —N(piperidine) | Oil | | 1.31, 9hs* |

TABLE I-continued (I)

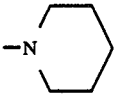

| Compound Number | X | Y | Z | n | NR¹R² | Melting Point (°C.) | Comments | ¹H NMR shifts (ppm from TMS) |
|---|---|---|---|---|---|---|---|---|
| 4 | t-C$_4$H$_9$ | H | H | 1 | 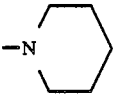 piperidine | Oil | | 6.44g, 1Hs+ 1.22, 9Hs* |
| 5 | t-C$_4$H$_9$ | H | H | 0 | piperidine | 39 | | 6.63, 1Hs+ 1.34, 9Hs* |
| 6 | H | t-C$_4$H$_9$ | H | 0 | piperidine | 53 | | 6.61, 1Hs+ 1.34, 9Hs* |
| 7 | t-C$_4$H$_9$ | H | H | 1 | 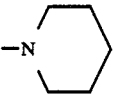 dimethylmorpholine | Oil | Cis-dimethyl morpholine | 6.28, 1Hs+ 1.24, 9Hs* |
| 8 | H | i-C$_3$H$_7$ | H | 1 | piperidine | | | |
| 9 | H | i-C$_3$H$_7$ | H | 1 | 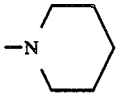 dimethylmorpholine | | Cis-dimethyl-morpholine | |
| 10 | i-C$_3$H$_7$ | H | H | 1 | piperidine | | | |
| 11 | i-C$_3$H$_7$ | H | H | 1 | 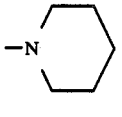 dimethylmorpholine | | Cis-dimethyl-morpholine | |
| 12 | i-C$_3$H$_7$ | H | CH$_3$ | 1 | 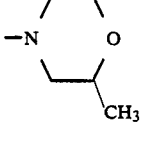 dimethylmorpholine | | Cis-dimethyl-morpholine | |

TABLE I-continued
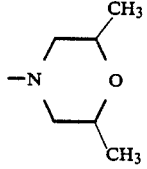
(I)
| Compound Number | X | Y | Z | n | NR¹R² | Melting Point (°C.) | Comments | ¹H NMR shifts (ppm from TMS) |
|---|---|---|---|---|---|---|---|---|
| 13 | H | i-C$_3$H$_7$ | CH$_3$ | 1 | 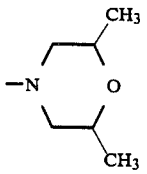 | | Cis-dimethyl-morpholine | |
| 14 | H | i-C$_3$H$_7$ | H | 0 | 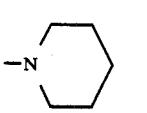 | | Cis-dimethyl-morpholine | |
| 15 | H | i-C$_3$H$_7$ | H | 0 | 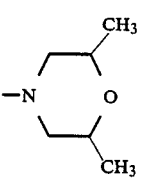 | | | |
| 16 | i-C$_3$H$_7$ | H | H | 0 | 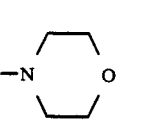 | | Cis-dimethyl-morpholine | |
| 17 | i-C$_3$H$_7$ | H | H | 0 | 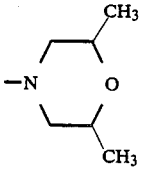 | | | |
| 18 | H | t-C$_5$H$_{11}$ | H | 1 | 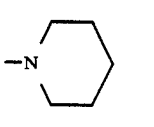 | | Cis-dimethyl-morpholine | |
| 19 | H | t-C$_5$H$_{11}$ | H | 1 | 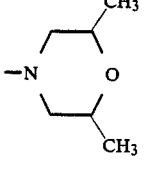 | | | |
| 20 | t-C$_5$H$_{11}$ | H | H | 1 | 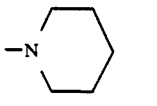 | | Cis-dimethyl-morpholine | |
| 21 | t-C$_5$H$_{11}$ | H | H | 1 | | | | |

TABLE I-continued

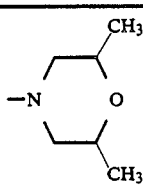
(I)

| Compound Number | X | Y | Z | n | NR¹R² | Melting Point (°C.) | Comments | ¹H NMR shifts (ppm from TMS) |
|---|---|---|---|---|---|---|---|---|
| 22 | H | $t$-C$_5$H$_{11}$ | H | 0 |  | | Cis-dimethyl-morpholine | |
| 23 | H | $t$-C$_5$H$_{11}$ | H | 0 | 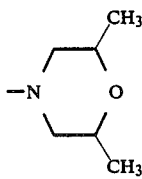 | | | |
| 24 | $t$-C$_5$H$_{11}$ | H | H | 0 |  | | Cis-dimethyl-morpholine | |
| 25 | $t$-C$_5$H$_{11}$ | H | H | 0 | 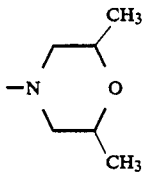 | | | |
| 26 | $t$-C$_4$H$_9$ | H | CH$_3$ | 1 | 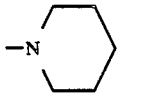 | | Cis-dimethyl-morpholine | |
| 27 | $t$-C$_4$H$_9$ | H | CH$_3$ | 1 | 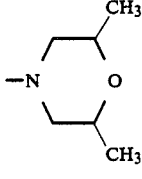 | | | |
| 28 | $t$-C$_4$H$_9$ | H | CH$_3$ | 0 | 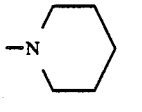 | | Cis-dimethyl-morpholine | |
| 29 | $t$-C$_4$H$_9$ | H | CH$_3$ | 0 | | | | |
| 30 | H | $t$-C$_4$H$_9$ | CH$_3$ | 0 | 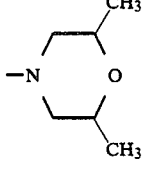 | | Cis-dimethyl-morpholine | |

TABLE I-continued (I)

| Compound Number | X | Y | Z | n | NR¹R² | Melting Point (°C.) | Comments | ¹H NMR shifts (ppm from TMS) |
|---|---|---|---|---|---|---|---|---|
| 31 | H | t-C₄H₉ | CH₃ | 0 | piperidino | | | |
| 32 | t-C₄H₉ | H | H | 1 | N(C₂H₅)₂ | | | |
| 33 | t-C₄H₉ | H | H | 0 | N(C₂H₅)₂ | | | |
| 34 | H | t-C₄H₉ | H | 1 | N(C₂H₅)₂ | | | |
| 35 | H | t-C₄H₉ | H | 0 | N(C₂H₅)₂ | | | |
| 36 | t-C₄H₉ | H | n-C₄H₉ | 1 | 2,6-dimethylmorpholino | | Cis-dimethylmorpholine | |
| 37 | t-C₄H₉ | H | n-C₄H₉ | 1 | piperidino | | | |
| 38 | H | t-C₄H₉ | n-C₄H₉ | 1 | 2,6-dimethylmorpholino | | Cis-dimethylmorpholine | |
| 39 | H | t-C₄H₉ | n-C₄H₉ | 1 | piperidino | | | |
| 40 | t-C₄H₉ | H | n-C₄H₉ | 0 | 2,6-dimethylmorpholino | | Cis-dimethylmorpholine | |

TABLE I-continued $$\underset{Y}{\overset{X}{\phantom{X}}}\underset{(CH_2)_n}{\overset{Z}{\phantom{Z}}}\underset{R^2}{\overset{CH_2}{\underset{N}{\phantom{N}}}}\overset{R^1}{\phantom{R^1}}$$ (I)

| Compound Number | X | Y | Z | n | NR¹R² | Melting Point (°C.) | Comments | ¹H NMR shifts (ppm from TMS) |
|---|---|---|---|---|---|---|---|---|
| 41 | t-C₄H₉ | H | n-C₄H₉ | 0 | —N(piperidine) | | | |
| 42 | H | t-C₄H₉ | n-C₄H₉ | 0 | —N(2,6-dimethylmorpholine) | | Cis-dimethyl-morpholine | |
| 43 | H | t-C₄H₉ | n-C₄H₉ | 0 | —N(piperidine) | | | |
| 44 | t-C₄H₉ | H | H | 1 | —N(n-C₄H₉)₂ | | | |
| 45 | H | t-C₄H₉ | H | 1 | —N(n-C₄H₉)₂ | | | |
| 46 | t-C₄H₉ | H | H | 1 | —N(pyrrolidine) | | | |
| 47 | H | t-C₄H₉ | H | 1 | —N(pyrrolidine) | | | |
| 48 | t-C₄H₉ | H | H | 1 | —N(piperazine)N—Ph | | | |
| 49 | H | t-C₄H₉ | H | 1 | —N(piperazine)N—Ph | | | |
| 50 | H | t-C₄H₉ | CH₃ | 1 | —N(2,6-dimethylmorpholine) | | Cis-dimethyl-morpholine | |

TABLE I-continued

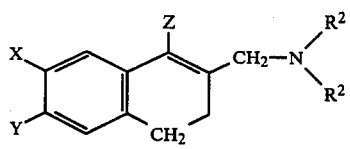
(I)

| Compound Number | X | Y | Z | n | NR¹R² | Melting Point (°C.) | Comments | ¹H NMR shifts (ppm from TMS) |
|---|---|---|---|---|---|---|---|---|
| 51 | H | t-C₄H₉ | H | 0 | (cis-2,6-dimethylmorpholine) | | Cis-dimethyl-morpholine | |
| 52 | t-C₄H₉ | H | H | 0 | (cis-2,6-dimethylmorpholine) | | Cis-dimethyl-morpholine | |

+proton on the double bond
*t-C₄H₉ protons

The present invention also provides novel compounds which possess fungicidal activity and are suitable for use as the active ingredient of the compositions hereinabove defined, the compounds having the general formula (II):

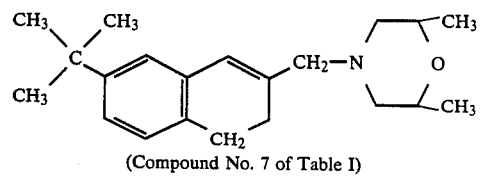
(II)

wherein X, Y, Z, R¹ and R² are as previously defined; these are thuse the compounds of formula (I) where n is equal to 1.

Preferred compounds of formula (II) are those where one of X and Y is a tert-butyl group. It is also preferred that Z should be hydrogen or a methyl group, and it is further preferred that the group, —NR¹R² should be a piperidine or a 2,6-dimethylmorpholine ring.

The invention particularly provides the following novel compounds:

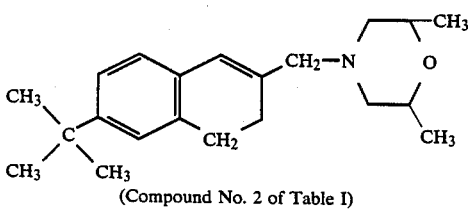
(Compound No. 2 of Table I)

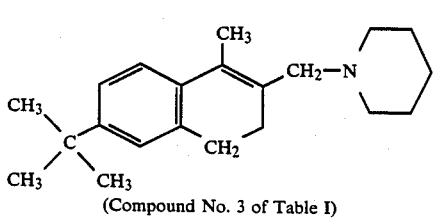
(Compound No. 3 of Table I)

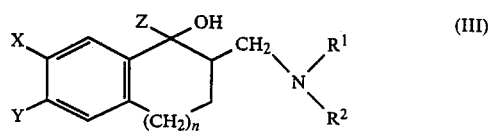
(Compound No. 7 of Table I)

Compounds of general formula (I) can be prepared by treatment of alcohols of general formula (III) wherein X, Y, Z, n, R¹ and R² are as defined above, with acid (eg. dilute sulphuric acid), preferably in the absence of a solvent and under reflux conditions.

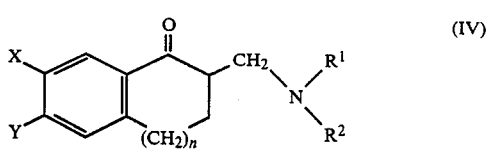
(III)

Alcohols of general formula (III) where Z is a hydrogen atom can be prepared by reduction of compounds of general formula (IV) with the usual reducing agents, for example sodium borohydride or lithium aluminium hydride.

(IV)

Where Z is an alkyl group, alcohols of general formula (III) may be prepared by treatment of ketones of general formula (IV) with the appropriate alkyl magnesium halide Grignard reagent or alkyl lithium in a suitable solvent (for example diethylether or tetrahydrofuran).

Ketones of general formula (IV) can be prepared by treating a compound of general formula (V) with formaldehyde and an amine of general formula $HNR^1R^2$ in the presence of an acidic catalyst under the normal conditions of the Mannich Reaction.

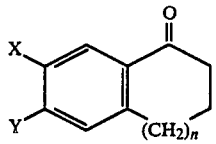

Compounds of general formula (V) can be prepared by oxidation of a hydrocarbon of general formula (VI) by a suitable oxidising agent, for example chromium trioxide in a solvent such as glacial acetic acid, (see, for example, J. W. Burnham, W. P. Duncan, and E. J. Eisenbraun, *Journal of Organic Chemistry* 1974, 39, 10, 1416).

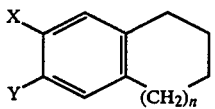

Alternatively they may be prepared by cyclisation of various substituted phenylcarboxylic acids (VII) by methods set out in the literature (see, for example, N. G. Bromby, A. T. Peters, and F. M. Rowe, *Journal of the Chemical Society* 1943, 1, 144).

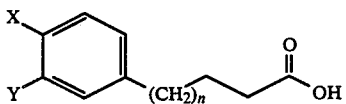

It will be appreciated that in certain instances oxidation of hydrocarbons of general formula (VI) in which X and Y represent different atoms or groups, with, for example, chromium trioxide in a solvent such as acetic acid can give rise to two isomeric ketones of general formula (V). Such isomeric ketones of general formula (V) can be conveniently separated by fractional distillation or by preparative high pressure liquid chromatography.

Compounds of general formula (VI) can be prepared by methods set out in the literature (see, for example, F. C. Whitmore and W. H. Jones, *Journal of American Chemical Society* 1943, 65, 2088). For example 6-tert-butyltetralin can be prepared by the Friedel-Crafts alkylation of tetralin using tert-butylchloride in a convenient solvent such as carbon disulphide using an appropriate catalyst, for example aluminium chloride.

Salts of the compounds of general formula (I) may be made by methods set out in the literature.

The compounds and salts are active fungicides, particularly against the diseases:

*Puccinia recondita,*
*Puccinia striiformis* and other rusts on wheat, *Puccinia hordei, Puccinia striiformis* and other rusts on barley, and rusts on other hosts e.g. coffee, apples, apples, vegetables and ornamental plants *Erysiphe graminis* (powdery mildew) on barley and wheat and other powdery mildews on various hosts such as
*Sphaerotheca fuliginea* on cucurbits (e.g. cucumber),
*Podosphaera leucotricha* on apples
*Cercospora arachidicola* on peanuts and other *Cercospora* species on for example sugar beet, bananas and soya beans
*Plasmopara viticola* on vines
*Venturia inaequalis* (scab) on apples.

Some of the compounds have also shown a broad range of activities against fungi in vitro. They may have activity against various post-harvest diseases on fruit (e.g. *Penicillium digatatum* and *italicum* on oranges and *Gloeosporium musarum* on bananas). Further some of the compounds may be active as seed dressings against: Fusarium spp., Septoria spp., Tilletia spp. (i.e. bunt, a seed borne disease of wheat), Ustilago spp., Helminthosporium spp. and *Pseudocercosporella herpotrichoides* on cereals, *Rhizoctonia solani* on cotton and *Corticium sasakii* on rice.

The compounds can move acropetally in the plant tissue. Moreover, the compounds can be volatile enough to be active in the vapour phase against fungi on the plant.

They may also be useful as industrial (as opposed to agricultural) fungicides, e.g. in the prevention of fungal attack on wood, hides, leather and especially paint films.

The active compounds may be used as such for fungicidal purposes but are more conveniently formulated into compositions for such usage. The invention thus provides a fungicidal composition comprising a compound of general formula (I) as hereinbefore defined or a salt; and, optionally, a carrier or diluent.

The invention also provides a method of combating fungi, which comprises applying to a plant, to seed of a plant, or to the locus of the plant or seed, a composition, compound, or salt, as hereinbefore defined.

The active compounds and salts can be applied in a number of ways, for example they can be applied directly to the foliage of a plant, or they can be applied also to bushes and trees, to seeds or to other medium in which plants, bushes or trees are growing or are to be planted, or they can be sprayed on, dusted on or applied as a cream or paste formulation, or they can be applied as a vapour; or as slow release granules. Application can be to any part of the plant, bush or tree, for example to the foliage, stems, branches or roots, or to soil surrounding the roots, or to the seed before it is planted; or to the soil generally, to paddy water or to hydroponic culture systems. The invention compounds may also be injected into plants or trees and they may also be sprayed onto vegetation using electrodynamic spraying techniques.

The term "plant" as used herein includes seedlings, bushes and trees. Furthermore, the fungicidal method of the invention includes preventative, protectant, prophylactic and eradicant treatment.

The compositions may be in the form of dusting powders or granules comprising the active ingredient and a solid diluent or carrier, for example fillers such as kaolin, bentonite, kieselguhr, dolomite, calcium carbonate, talc, powdered magnesia, Fuller's earth, gypsum, Hewitt's earth, diatomaceous earth and China clay. Such granules can be preformed granules suitable for application to the soil without further treatment. These granules can be made either by impregnating pellets of filler with the active ingredient or by pelleting a mixture of the active ingredient and powdered filler. Compositions for dressing seed, for example, may comprise an agent (for example a mineral oil) for assisting the adhesion of the composition to the seed; alternatively the active ingredient can be formulated for seed dressing purposes using an organic solvent (for example N-methylpyrrolidone or dimethylformamide).

The compositions may also be in the form of dispersible powders, granules or grains comprising a wetting agent to facilitate the dispersion in liquids of the powder or grains which may contain also fillers and suspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable organic solvents are ethylene dichloride, isopropyl alcohol, propylene glycol, diacetone alcohol, toluene, kerosene, methylnaphthalene, the xylenes, trichloroethylene, furfuryl alcohol, tetrahydrofurfuryl alcohol, and glycol ethers (eg. 2-ethoxyethanol and 2-butoxyethanol).

The compositions to be used as sprays may also be in the form of aerosols wherein the formulation is held in a container under pressure in the presence of a propellant, eg. fluorotrichloromethane or dichlorodifluoromethane.

The compounds can be mixed in the dry state with a pyrotechnic mixture to form a composition suitable for generating in enclosed spaces a smoke containing the compounds.

Alternatively, the active compounds may be used in a micro-encapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The compounds can be used as mixtures with fertilisers (eg. nitrogen-, potassium- or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising the compound of general formula (I) or a salt or metal complex thereof.

The compositions may also be in the form of liquid preparations for use as dips or sprays which are generally aqueous dispersions or emulsions containing the active ingredient in the presence of one or more surfactants eg. wetting agent(s), dispersing agent(s), emulsifying agent(s) or suspending agent(s); or which are spray formulations of the kind suitable for use in electrodynamic spraying techniques. The foregoing agents can be cationic, anionic or non-ionic agents. Suitable cationic agents are quaternary ammonium compounds, for example cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butyl-naphthalene sulphonate, and a mixture of sodium diisopropyl- and triisopropyl-naphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents are the partial esters derived from long chain fatty acids and hexitol anhydrides, and condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), and the concentrate is to be diluted with water before use. These concentrates often should be able to withstand storage for prolonged periods and after such storage be capable of dilution with water in order to form aqueous preparations which remain homogeneous for a sufficient time to enable them to be applied by conventional and electrodynamic spray equipment. The concentrates may conveniently contain up to 95%, suitably 10–85%, for example 25–60%, by weight of the active ingredient(s). These concentrates suitably contain organic acids (eg. alkaryl or aryl sulphonic acids such as xylenesulphonic acid or dodecyl benzenesulphonic acid) since the presence of such acids can increase the solubility of the active ingredient(s) in the polar solvents often used in the concentrates. The concentrates suitably contain also a high proportion of surfactants so that sufficiently stable emulsions in water can be obtained. After dilution to form aqueous preparations, such preparations may contain varying amounts of the active ingredient(s) depending upon the intended purpose, but an aqueous preparation containing 0.0005% or 0.01% to 10% by weight of active ingredient(s) may be used.

The compositions of this invention can comprise also other compound(s) having biological activity, eg. compounds having similar or complementary fungicidal activity or compounds having plant growth regulating, herbicidal or insecticidal activity.

The other fungicidal compound can be, for example, one which is capable of combating ear diseases of cereals (eg. wheat) such as Septoria, Gibberella and Helminthosporium spp., seed and soil borne diseases and downy and powdery mildews on grapes and powdery mildew and scab on apple etc. These mixtures of fungicides can have a broader spectrum of activity than the compound of general formula (I) alone; further the other fungicide can have a synergistic effect on the fungicidal activity of the compound of general formula (I). Examples of the other fungicidal compound are carbendazim, benomyl, thiophanate-methyl, thiabendazole, fuberidazole, etridazole, dichlofluanid, cymoxanil, oxadixyl, ofurace, metalaxyl, furalaxyl, benalaxyl, fosetyl aluminium, fenarimol, iprodione, procymidone, vinclozolin, penconazole, myclobutanil, R0151297, S3308, pyrazophos, ethirimol, ditalimfos, tridermorph, triforine, nuarimol, triazbutyl, guazatine, propiconazole, prochloraz, flutriafol, chlortriafol i.e. the chemical 1-(1,2,4-triazol-1-yl)-2-(2,4-dichlorophenyl)-hexan-2-ol, DPX H6573(1-((bis-4-fluorophenyl)methylsilyl)-methyl-1H-1,2,4-triazole, triadimefon, triadimenol, dichlobutrazol, fenpropimorph, fenpropidin, chlorozolinate, diniconazol, imazalil, fenfuram, carboxin, oxycarboxin, methfuroxam, dodemorph, BAS 454, blasticidin S, kasugamycin, edifenphos, kitazin P, cycloheximide, phthalide, probenazole, isoprothiolane, tricyclazole, pyroquilan, chlorbenzthiazone, neoasozin, polyoxin D, validamycin A, repronil, flutolanil, pencycuron, diclomezine, phenazin oxide, nickel dimethyldithiocarbamate, techlofthalam, bitertanol, bupirimate, etaconazole, streptomycin, cypofuram, biloxazol, quinomethionate, dimethirimol, 1-(2-cyano-2-methoxyiminoacetyl)-3-ethyl urea, fenapanil, tolclofosmethyl, pyroxyfur, polyram, maneb, mancozeb, captafol, chlorothalonil, anilazine, thiram, captan, folpet, zineb, propineb, sulphur, dinocap, binapactryl, nitrothalisopropyl, dodine, dithianon, fentin hydroxide, fentin acetate, tecnazene, quintozene, dichloran, copper containing compounds such as copper oxychloride, copper sulphate and Bordeaux mixture, and organomercury compounds.

The compounds of general formula (I) can be mixed with soil, peat or other rooting media for the protection of plants against seed-borne, soil-borne or foliar fungal diseases.

Suitable insecticides which may be incorporated in the compositions of the invention include pirimicarb, dimethoate, demeton-s-methyl, formothion, carbaryl, isoprocarb, XMC, BPMC, carbofuran, carbosulfan, diazinon, fenthion, fenitrothion, phenthoate, chlorpyrifos, isoxathion, propaphos, monocrotophos, buprofezin, ethroproxyfen and cycloprothrin.

Plant growth regulating compounds which may be used in the invention compositions are compounds which control weeds or seedhead formation, or selectively control the growth of less desirable plants (e.g. grasses).

Examples of suitable plant growth regulating compounds for use with the invention compositions and compounds are the gibberellins (e.g. $GA_3$, $GA_4$ or $GA_7$), the auxins (e.g. indoleacetic acid, indolebutyric acid, naphthoxyacetic acid or naphthylacetic acid), the cytokinins (e.g. kinetin, diphenylurea, benzimidazole, benzyladenine or benzylaminopurine), phenoxyacetic acids (e.g. 2,4-D or MCPA), substituted benzoic acids (e.g. triiodobenzoic acid), morphactins (e.g. chlorfluoroecol), maleic hydrazide, glyphosate, glyphosine, long chain fatty alcohols and acids, dikegulac, paclobutrazol, flurprimidol, fluoridamid, mefluidide, substituted quaternary ammonium and phosphonium compounds (e.g. chloromequat chlorphonium or mepiquatchloride), ethephon, carbetamide, methyl-3,6-dichloroanisate, daminozide, asulam, abscisic acid, isopyrimil, 1-(4-chlorophenyl)-4,6-dimethyl-2-oxo-1,2-dihydropyridine-3-carboxylic acid, hydroxybenzonitriles (e.g. bromoxynil), difenzoquat, benzoylprop-ethyl 3,6-dichloropicolinic acid, fenpentezol, inabenfide, triapenthenol and tecnazene.

The following Examples illustrate the invention; the temperatures are given in degrees Centigrade (°C.).

EXAMPLE 1

This Example illustrates the preparation of 6-tert-butyl-3-piperidinomethyl-1,2-dihydronaphthalene (Compound number 4 of Table I). Piperidine hydrochloride (8.9 g, 0.073 mol), 7-tert-butyl-1,2,3,4-tetrahydronaphthalen-1-one (7.0 g, 0.035 mol) and paraformaldehyde (2.2 g, 0.073 mol) were refluxed together in ethanol (150 ml) along with concentrated hydrochloric acid (1 ml) as a catalyst for 16 hours. The reaction mixture was concentrated under reduced pressure and the residue dissolved in water then extracted with diethyl ether. The resulting aqueous solution was neutralized with sodium bicarbonate and extracted with diethyl ether (2×200 ml); the ethereal extracts were dried over magnesium sulphate and concentrated under reduced pressure to give 7-tert-butyl-2-piperidinomethyl-1,2,3,4-tetrahydronaphthalen-1-one (4.5 g, 43% yield) as a buff coloured solid melting at 62°-3°. The 7-tert-butyl-2-piperidinomethyl-1,2,3,4-tetrahydronaphthalen-1-one (4.5 g, 0.015 mol) was dissolved in methanol (100 ml) and sodium borohydride (0.6 g, 0.016 mol) was added portionwise over 30 minutes at room temperature. It was stirred for 3 hours at room temperature then the methanol was evaporated under reduced pressure and the residue treated with water (100 ml) and extracted with ether (2×100 ml) which was washed with brine, dried over magnesium sulphate and evaporated under reduced pressure to give a viscous oil (4.0 g) which crystallised on standing. Separation by column chromatography on silica gel (Merck 60) using a gradient elution of petrol 60°-80° to ethyl acetate gave the alcohol as two isomers:

(A) the faster running isomer as a white crystalline solid (1.95 g, mpt 88°-90°), $^1H$ nmr (CDCl$_3$): δ4.68, J=9.2 Hz (1 proton) the trans-7-tert-butyl-2-piperidinomethyl-1,2,3,4-tetrahydronaphthalen-1-ol.

(B) the slower running isomer a white crystalline solid (350 mg, mpt 88°-90°) $^1H$ nmr (CDCl$_3$): δ4.86, J=4 Hz (1 proton) the cis-7-tert-butyl-2-piperidinomethyl-1,2,3,4-tetrahydronaphthalen-1-ol.

The trans-7-tert-butyl-2-piperidinomethyl-1,2,3,4-tetrahydronaphthalen-1-ol (2.6 g) was dissolved in 70 mls of 10% dilute sulphuric acid and refluxed for 2 hours. After cooling the solution was washed with ether then neutralized with sodium bicarbonate, this was extracted with diethyl ether, dried over magnesium sulphate and evaporated under reduced pressure to give the title compound (2.0 g 81% yield) as a clear pale yellow oil. $^1H$ nmr (CDCl$_3$): δ6.44 (1 proton).

EXAMPLE 2

This Example illustrates the preparation of 7-tert-butyl-4-methyl-3-piperidinomethyl,1,2-dihydronaphthalene (Compound number 3 of Table I). Piperidine hydrochloride (12.6 g 0.103 mol), 6-tert-butyl-1,2,3,4-tetrahydronaphthalen-1-one (80.0 g, 0.04 mol) and paraformaldehyde (2.64 g, 0.088 mol) were refluxed in ethanol (200 ml) with concentrated hydrochloric acid (1 ml) as a catalyst for 48 hours. The reaction mixture was concentrated under reduced pressure and the residue dissolved in water then extracted with diethyl ether. The resulting aqueous solution was neutralized with sodium bicarbonate and extracted with diethyl ether (2×200 ml); the ethereal extracts were dried over magnesium sulphate and concentrated under reduced pressure to give 6-tert-butyl-2-piperidinomethyl-1,2,3,4-tetrahydronaphthalen-1-one (10.0 g 83% yield) melting at 47°-9°.

6-Tert-butyl-2-piperidinomethyl-1,2,3,4-tetrahydronaphthalen-1-one (4.4 g, 0.015 mol) in diethyl ether (40 ml) was added to an ethereal solution of methylmagnesium iodide [prepared from methyl iodide (1.9 ml, 0.03 mol) and magnesium (0.72 g, 0.03 mol)] at such a rate as to maintain reflux. It was refluxed for 1 hour, cooled and treated with saturated ammonium chloride solution (100 ml) and refluxed for 30 minutes. The ether was separated and the aqueous extracted with further ether, the combined extracts were dried over magnesium sulphate and evaporated to give a solid residue. Purification by column chromatography using silica gel with ethyl acetate: petroleum 60°-80°, 3:7 gave 6-tert-butyl-1-methyl-2-piperidinomethyl-1,2,3,4-tetrahydronaphthalen-1-ol (3.9 g, 82% yield) a white solid melting at 113°-4°. 6-tert-butyl-1-methyl-2-piperidinomethyl-1,2,3,4-tetrahydronaphthalen-1-ol (3.7 g, 0.012 mol) was refluxed in dilute sulphuric acid (50 ml, 10%) for 45 minutes. After cooling it was neutralized with sodium hydroxide, extracted with ether, dried over magnesium sulphate and evaporated under reduced pressure to give the title compound (3.5 g, 98% yield) as a clear oil.

EXAMPLE 3

This Example illustrates the preparation of 7-tert-butyl-3-cis-(2,6-dimethylmorpholinomethyl)-1,2-dihydronaphthalene (Compound No. 2 in Table I). 2,6-Dimethylmorpholine hydrochloride (12.1 g, 0.08 mol), 6-tert-butyl-1,2,3,4-tetrahydronaphthalen-1-one (8.1 g, 0.04 mol) and paraformaldehyde (2.4 g, 0.08 mol) were refluxed together in ethanol (150 ml) with concentrated hydrochloric acid (1 ml) as a catalyst for 16 hours. The reaction mixture was concentrated under reduced pressure and the residue dissolved in water then extracted with diethyl ether. The resulting aqueous solution was neutralised with sodium bicarbonate and extracted with diethyl ether (2×200 ml); the ethereal extracts were dried over anhydrous magnesium sulphate and concentrated under reduced pressure to give an orange oil. This oil was purified by hplc (silica eluted with ethyl acetate/petroleum ether 1:1) to give 6-tert-butyl-2-cis-(2,6-dimethylmorpholinomethyl)-1,2,3,4-tetrahydronaphthalen-1-one (5.1 g, 39%).

6-Tert-butyl-2-cis-(2,6-dimethylmorpholinomethyl)-1,2,3,4-tetrahydronaphthalen-1-one (4.6 g, 0.014 mol) was dissolved in methanol (100 ml) and sodium borohydride (0.5 g, 0.013 mol) was added portionwise over 30 minutes at room temperature. It was stirred for 3 hours at room temperature then the methanol was evaporated under reduced pressure and the residue treated with water (100 ml) and extracted with ether (2×100 ml) which was washed with brine, dried over magnesium sulphate and evaporated under reduced pressure to give an oil. This was purified by column chromatography (silica eluted with ethyl acetate/petroleum ether 2:3) to give trans-6-tert-butyl-cis-(2,6-dimethylmorpholinomethyl)-1,2,3,4-tetrahydronaphthalen-1-ol (2.0 g, 43%) as a clear oil.

The trans-6-tert-butyl-cis-(2,6-dimethylmorpholinomethyl)-1,2,3,4-tetrahydronaphthalen-1-ol (0.7 g, 00021 mol) was dissolved in 10% sulphuric acid (30 ml) and refluxed for 2 hours. After cooling the solution was washed with ether then neutralised with sodium bicarbonate; this was extracted with diethyl ether dried over anhydrous magnesium sulphate and evaporated under reduced pressure to give the title compound (0.6 g, 90%) as a clear oil. $^1$H NMR (CDCl$_3$): δ6.23 (1 proton).

EXAMPLE 4

An emulsifiable concentrate is made up by mixing the ingredients, and stirring the mixture until all the constituents are dissolved.

| | |
|---|---|
| Compound No 5 of Table I | 10% |
| Isophorone | 25% |
| Calcium dodecylbenzenesulphonate | 5% |
| Nonylphenolethoxylate (13 moles ethylene oxide) | 10% |
| Alkyl benzenes | 50% |

EXAMPLE 5

The active ingredient is dissolved in methylene dichloride and the resultant liquid sprayed onto the granules of attapulgite clay. The solvent is then allowed to evaporate to produce a granular composition.

| | |
|---|---|
| Compound No 6 of Table I | 5% |
| Attapulgite granules | 95% |

EXAMPLE 6

A composition suitable for use as a seed dressing is prepared by grinding and mixing the three ingredients.

| | |
|---|---|
| Compound No 5 of Table I | 50% |
| Mineral oil | 2% |
| China clay | 48% |

EXAMPLE 7

A dustable powder is prepared by grinding and mixing the active ingredient with talc.

| | |
|---|---|
| Compound No 6 of Table I | 5% |
| Talc | 95% |

EXAMPLE 8

A suspension concentrate is prepared for chemicals which are largely insoluble solids by ball milling, for example, the constituents set out below, to form an aqueous suspension of the ground mixture with water.

| | |
|---|---|
| Compound No 5 of Table I | 40% |
| Sodium lignosulphonate | 10% |
| Bentonite clay | 1% |
| Water | 49% |

This formulation can be used as a spray by diluting into water or applied directly to seed.

EXAMPLE 9

A wettable powder formulation is made by mixing together the ingredients set out below and then grinding the mixture until all are thoroughly mixed.

| | |
|---|---|
| Compound No 6 of Table I | 25% |
| Sodium lauryl sulphate | 2% |
| Sodium lignosulphonate | 5% |
| Silica | 25% |
| China clay | 43% |

EXAMPLE 10

A Col formulation was prepared by ball-milling the constituents set out below and then forming an aqueous suspension of the ground mixture with water.

| | |
|---|---|
| Compound No 5 of Table I | 40% |
| "Dispersol" T | 10% |
| "Lubrol" APN5 | 1% |
| Water | |

EXAMPLE 11

A dispersible powder formulation was made by mixing together the ingredients set out below and then grinding the mixture until all were thoroughly mixed.

| Compound No 6 of Table I | 25% |
|---|---|
| "Aerosol" OT/B | 2% |
| "Dispersol" A.C. | 5% |
| China clay | 28% |
| Silica | 40% |

In Examples 4 to 11 the proportions of the ingredients given are by weight. The remaining compounds of Table I were all similarly formulated as per Examples 4 to 11.

There now follows an explanation of the compositions or substances represented by the various Trade Marks mentioned above.

DISPERSOL T and AC: a mixture of sodium sulphate and a condensate of formaldehyde with sodium naphthalene sulphonate LUBROL APN5: a condensate of nonyl phenol (1 mole) with naphthalene oxide (5.5 moles)

AEROSOL OT/B: dioctyl sodium sulphosuccinate

EXAMPLE 12

The compounds were tested against a variety of mainly foliar fungal diseases of plants. The techniques employed were as follows.

For all tests the plants were grown in John Innes Potting Compost (No. 1 or 2) in 4 cm diameter minipots. The test compounds were formulated either by bead milling with aqueous Dispersol T or as a solution in acetone or acetone/ethanol which was diluted to the required concentration immediately before use. The solutions or suspensions (100 ppm ai.) were sprayed on the foliage and applied to the roots of the plant via the soil. The sprays were applied to maximum retention and the root drenches to a final concentration equivalent to approximately 40 ppm ai./dry soil. Tween 20, to give a final concentration of 0.05%, was added when the sprays were applied to cereals. (a.i. means "active ingredient").

Most were protectant tests where the compound was applied to the soil and roots and to the foliage one or two days before the plant was inoculated with the pathogen. (*Erysiphe graminis* was a one day eradicant test). The foliar pathogens were applied by spraying as spore suspensions onto the leaves of the test plants.

After inoculation, the plants were placed in an appropriate environment to allow infection to proceed and then incubated until the disease was ready for assessment. The period between inoculation and assessment varied from four to fourteen days according to the disease and the environment.

Disease control was recorded using the following grading system:
4=no disease
3=trace to 5% of disease on untreated plants
2=6–25% of disease on untreated plants
1=26–59% of disease on untreated plants
0=60–100% of disease on untreated plants The results are shown in Table II.

TABLE II

| COMPOUND NUMBER | PUCCINIA RECONDITA (WHEAT) | VENTURIA INAEQUALIS (APPLES) | CERCOSPORA ARACHIDICOLA (PEANUTS) | PLASMOPARA VITICOLA (VINES) | ERYSIPHE GRAMINIS HORDEI (BARLEY) |
|---|---|---|---|---|---|
| 1 | 2 | 0 | 0 | 0 | 4 |
| 2 | 0 | 3 | 4 | 0 | 4 |
| 3 | 3 | 0 | 4 | 0 | 4 |
| 4 | 0 | 0 | 2 | 0 | 4 |
| 5 | 3 | 2 | 0 | 1 | 4 |
| 6 | 2 | 0 | 0 | 4 | 0 |
| 7 | 2 | 4 | 4 | 0 | 4 |

We claim:

1. A fungicidal composition comprising a diluent or carrier and as an active ingredient (a) a compound having the general formula $$\text{(I)}$$

or a stereoisomer thereof, wherein one of X and Y represents hydrogen and the other represents the group $$-\underset{\underset{CH_3}{|}}{\overset{\overset{CH_3}{|}}{C}}-R$$

in which R is hydrogen, methyl or ethyl; Z represents an alkyl group containing from one to four carbon atoms; $R^1$ and $R^2$ together with the adjacent nitrogen atom represent a piperidine ring optionally substituted by one or more alkyl, aryl, hydroxy, alkoxy, aryloxy or aralkyl groups; and n is 1; or (b) an acid addition salt of such a compound.

2. A composition as claimed in claim 1, wherein in the active compound one of X and Y is a tert-butyl group.

3. A composition as claimed in claim 1, wherein the active compound has the formula:

4. A method of combating fungi which comprises applying to a plant, to seed of a plant or to the locus of a plant or seed, a fungicidal composition as claimed in any one of claims 1, 2, or 3.

* * * * *